(12) United States Patent (10) Patent No.: US 7,787,110 B2
Raguin et al. (45) Date of Patent: Aug. 31, 2010

(54) DIFFRACTIVE IMAGING SYSTEM AND METHOD FOR THE READING AND ANALYSIS OF SKIN TOPOLOGY

(75) Inventors: Daniel H. Raguin, Acton, MA (US);
David A. Waldman, Concord, MA (US);
Phillip H. Malyak, Canton, MA (US);
John S. Berg, Franklin, MA (US);
Richard T. Ingwall, Newton, MA (US)

(73) Assignee: Aprilis, Inc., Maynard, MA (US)

( * ) Notice: Subject to any disclaimer, the term of this patent is extended or adjusted under 35 U.S.C. 154(b) by 695 days.

(21) Appl. No.: 11/251,062

(22) Filed: Oct. 14, 2005

(65) Prior Publication Data

US 2006/0119837 A1 Jun. 8, 2006

Related U.S. Application Data

(60) Provisional application No. 60/619,459, filed on Oct. 16, 2004.

(51) Int. Cl.
*G06K 9/24* (2006.01)
(52) U.S. Cl. .................................. 356/71; 382/124
(58) Field of Classification Search .................. 356/71; 382/124

See application file for complete search history.

(56) References Cited

U.S. PATENT DOCUMENTS 3,864,042 A * 2/1975 Leventhal .................... 356/71
4,120,585 A * 10/1978 DePalma et al. .............. 356/71
4,728,186 A * 3/1988 Eguchi et al. ................ 356/71
5,621,516 A * 4/1997 Shinzaki et al. .............. 356/71
5,986,746 A 11/1999 Metz et al.

(Continued)

FOREIGN PATENT DOCUMENTS

EP 0045916 2/1982
EP 0194783 9/1986

OTHER PUBLICATIONS

International Search Report PCT/US05/037007. Search report dated Jan. 25, 2006.

(Continued)

*Primary Examiner*—Gregory J Toatley, Jr.
*Assistant Examiner*—Rebecca C Slomski
(74) *Attorney, Agent, or Firm*—Weaver Austin Villeneuve & Sampson LLP

(57) ABSTRACT

An apparatus and a method for acquiring an image of skin topology. The apparatus comprises at least one light source, configured to form a source beam; at least one illuminating diffractive optical element (DOE) disposed in the optical path of the source beam, configured to diffract the source beam, thereby forming an illuminating beam; a skin contact surface, disposed in the optical path of the illuminating beam, configured to at least partially reflect the illuminating beam at regions of the boundary between the skin contact surface and skin that are not in contact with the skin contact surface, thereby forming a reflected beam; at least one imaging diffractive optical element (DOE), disposed in the optical path of the reflected beam, configured to diffract the reflected light beam, thereby forming an image beam; and a sensor array, configured to receive at least a portion of the image beam and thereby to detect the acquired image.

45 Claims, 8 Drawing Sheets

U.S. PATENT DOCUMENTS 6,665,427 B1* 12/2003 Keagy et al. ................ 382/124
2004/0240712 A1* 12/2004 Rowe et al. ................. 382/124
2004/0252867 A1* 12/2004 Lan et al. ................... 382/124

OTHER PUBLICATIONS

International Written Opinion PCT/US05/037007. Opinion dated Jan. 25, 2006.

L.A. Brunsting, C. Sheard, "The Color of the Skin as Analyzed by Spectrophotometric Methods: II. The Role of Pigmentation." Journal of Clinical Investigation (1929) pp. 574-592, vol. 7.

G.L. Thomas, T.E. Reynoldson, "Some Observations on Fingerprint Deposits" J. Phys. D: Appl. Phys. pp. 724-729, vol. 8. (1975).

Elli Angelopoulou. "Understanding the Color of Human Skin" SPIE SPIE Press, pp. 243-251. vol. 4299, May 2001.

* cited by examiner

DIFFRACTIVE IMAGING SYSTEM AND METHOD FOR THE READING AND ANALYSIS OF SKIN TOPOLOGY

RELATED APPLICATIONS

This application claims the benefit of U.S. Provisional Application No. 60/619,459, filed on Oct. 16, 2004. The entire teachings of the above application are incorporated herein by reference.

BACKGROUND OF THE INVENTION

Growing concerns regarding domestic security have created a critical need to positively identify individuals as legitimate holders of credit cards, driver's licenses, passports and other forms of identification such as those for the military or drivers of hazardous materials, or school teachers, etc. The ideal identification process is reliable, fast, and relatively inexpensive.

A well-established method for identification is to compare a fingerprint with a previously obtained authentic fingerprint of the individual. Fingerprints have traditionally been collected by rolling an inked finger on a white paper. Attempts to employ an electronically imaged fingerprint method use, as a key component, a solid-state device such as a capacitive or optical sensor to capture the fingerprint image in a digital format.

A typical fingerprint comprises a pattern of ridges separated by valleys, and a series of pores that are located along the ridges. The ridges are usually 100 to 300 µm wide and can extend in a swirl-like pattern for several mm to one or more cm. These ridges are separated by valleys with a typical ridge-valley period of approximately 250-500 µm. Pores, roughly circular in cross section, range in diameter from about 60 µm to 240 µm and are aligned along the ridges and can be isolated or grouped into two or more abutting or near abutting features. There are typically more than 400 pores within a fingerprint region with a frequency of occurrence of about 21 pores/cm of ridge length. Almost all present-day fingerprint identification procedures use only ridge/valley minutiae patterns. These are simplified and identified as a pattern of ridge/valley features such as end points, deltoids, bifurcations, crossover points, and islands, all together referred to as minutiae. Typically, a relatively large area of the fingerprint is required in order to obtain enough unique minutiae features, for example, at least 0.50×0.50 inches. Most modern fingerprint imagers therefore use up to one full inch square or even larger, in order to obtain enough features to perform a useful means of identification. Fingerprints are compared using primarily this simplified description of the minutiae patterns.

Due to the more demanding resolution requirements necessary to successfully image friction ridge detail and/or pores, and the requirements for enrolling and analyzing such high resolution imagines, there are no commercial devices available today that use friction ridge detail and pores for fingerprint identification, even though there are typically 7 to 10 ten times as many pores as minutiae in a given fingerprint area. A typical fingerprint image as small as 0.1×0.1 inches may only contain 2-5 minutiae points, not enough to reliably identify a unique individual. The same area, however, may typically contain as many as 40 to 50 pores and several thousand ridge contour details, which along with a few minutiae points can positively identify an individual reliably.

SUMMARY OF THE INVENTION

Most optical designs proposed for creating fingerprint images suffer important limitations that reduce their usefulness in real life applications. Many designs are not suitable, for example, to resolve pore patterns or fine detail of the contour of the intersection of ridges and valleys in the fingerprint. Other designs produce distorted images that complicate fingerprint correlation, such as due to trapezoidal distortions, or due to presence of latent fingerprints, or due to the presence of moisture on the skin surface, and still other designs are too bulky or delicate for convenient use in the field.

Accordingly, there is a need for a compact, high-resolution device that reliably operates over a broad range of temperatures.

The present invention is a method and an apparatus for imaging and analyzing the surface topology of two-dimensional (2-D) area of the skin.

In one embodiment, the present invention is an apparatus for acquiring an image of skin topology. The apparatus comprises at least one light source, configured to form a source beam; at least one illuminating diffractive optical element (DOE) disposed in the optical path of the source beam, configured to diffract the source beam, thereby forming an illuminating beam; a skin contact surface, disposed in the optical path of the illuminating beam, configured to at least partially reflect the illuminating beam at regions of the boundary between the skin-contact surface and skin that are not in contact with the skin contact surface, thereby forming a reflected beam; at least one imaging diffractive optical element (DOE), disposed in the optical path of the reflected beam, configured to diffract the reflected light beam, thereby forming an image beam; and a sensor array, configured to receive at least a portion of the image beam and thereby to detect the acquired image.

In another embodiment, the present invention is a method of acquiring an image of skin topology. The method comprises directing a source beam from a light source to at least one illuminating diffractive optical element (DOE), thereby diffracting the source beam and forming an illuminating beam; directing the illuminating beam at a skin contact surface, configured to at least partially reflect the illuminating beam when the skin contact surface is not in contact with skin, thereby at least partially reflecting the illuminating beam and forming a reflected beam; directing the reflected beam to at least one imaging diffractive optical element (DOE), thereby diffracting the reflected light beam and forming an image beam; and directing the image beam at a sensor array, thereby detecting the acquired image.

In another embodiment, the present invention is an apparatus for acquiring an image of skin topology. The apparatus comprises light generating means for forming a source beam; illuminating diffractive means disposed in the optical path of the source beam, for diffracting the source beam and thereby forming an illuminating beam; skin contacting means, disposed in the optical path of the illuminating beam, for at least partially reflecting the illuminating beam at regions of the boundary between the skin contacting means and skin not in contact with the skin contacting means, thereby forming a reflected beam; at least one imaging diffractive means, disposed in the optical path of the reflected beam, for diffracting the reflected light beam and thereby forming an image beam; and detection means for receiving at least a portion of the image beam and thereby detecting the acquired image.

In one embodiment, the present invention is an apparatus for acquiring an image of skin topology. The apparatus comprises light generating means for forming a source beam; illuminating diffractive means, disposed in the optical path of the source beam, for diffracting the source beam and thereby forming an illuminating beam; skin contact means, disposed in the optical path of the illuminating beam, for at least partially reflecting the illuminating beam at regions of the boundary between the skin contact means and skin that are not in contact with the skin contact means, thereby forming a reflected beam; at least one imaging diffractive means, disposed in the optical path of the reflected beam, for diffracting the reflected light beam and thereby forming an image beam; and detection means for receiving at least a portion of the image beam and thereby detecting the acquired image.

In another embodiment, an apparatus of the present invention for acquiring an image of skin topology comprises at least one light source, configured to form a source beam; at least one illuminating diffractive optical element (DOE) disposed in the optical path of the source beam, configured to diffract the source beam, thereby forming an illuminating beam; a skin contact surface, disposed in the optical path of the illuminating beam, configured to at least partially reflect the illuminating beam at regions of the boundary between the skin contact surface and skin that are not in contact with the skin contact surface, thereby forming a reflected beam; at least one imaging diffractive optical element (DOE), disposed in the optical path of the reflected beam, configured to diffract the reflected light beam, thereby forming an image beam; and a sensor array, configured to receive at least a portion of the image beam and thereby to detect the acquired image.

In another embodiment, the present invention is a method of acquiring an image of skin topology. The method comprises directing a source beam from a light source to at least one illuminating diffractive optical element (DOE), thereby diffracting the source beam and forming an illuminating beam; directing the illuminating beam at a skin contact surface, configured to at least partially reflect the illuminating beam when the skin contact surface is not in contact with skin, thereby at least partially reflecting the illuminating beam and forming a reflected beam; directing the reflected beam to at least one imaging diffractive optical element (DOE), thereby diffracting the reflected light beam and forming an image beam; and directing the image beam at a sensor array, thereby detecting the acquired image.

The apparatus and the method of the instant invention produce undistorted images of high resolution by employing a compact design. Specifically, the apparatus of the present invention produces a high-contrast, high-resolution image by illuminating the image surface at a shallow angle, thus inducing total internal at the interface of the imaged surface and the surface that the imaged surface is in contact with. Apparatus of the present invention is portable and can work in a wide range of temperatures due to employing diffractive holographic optical elements.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
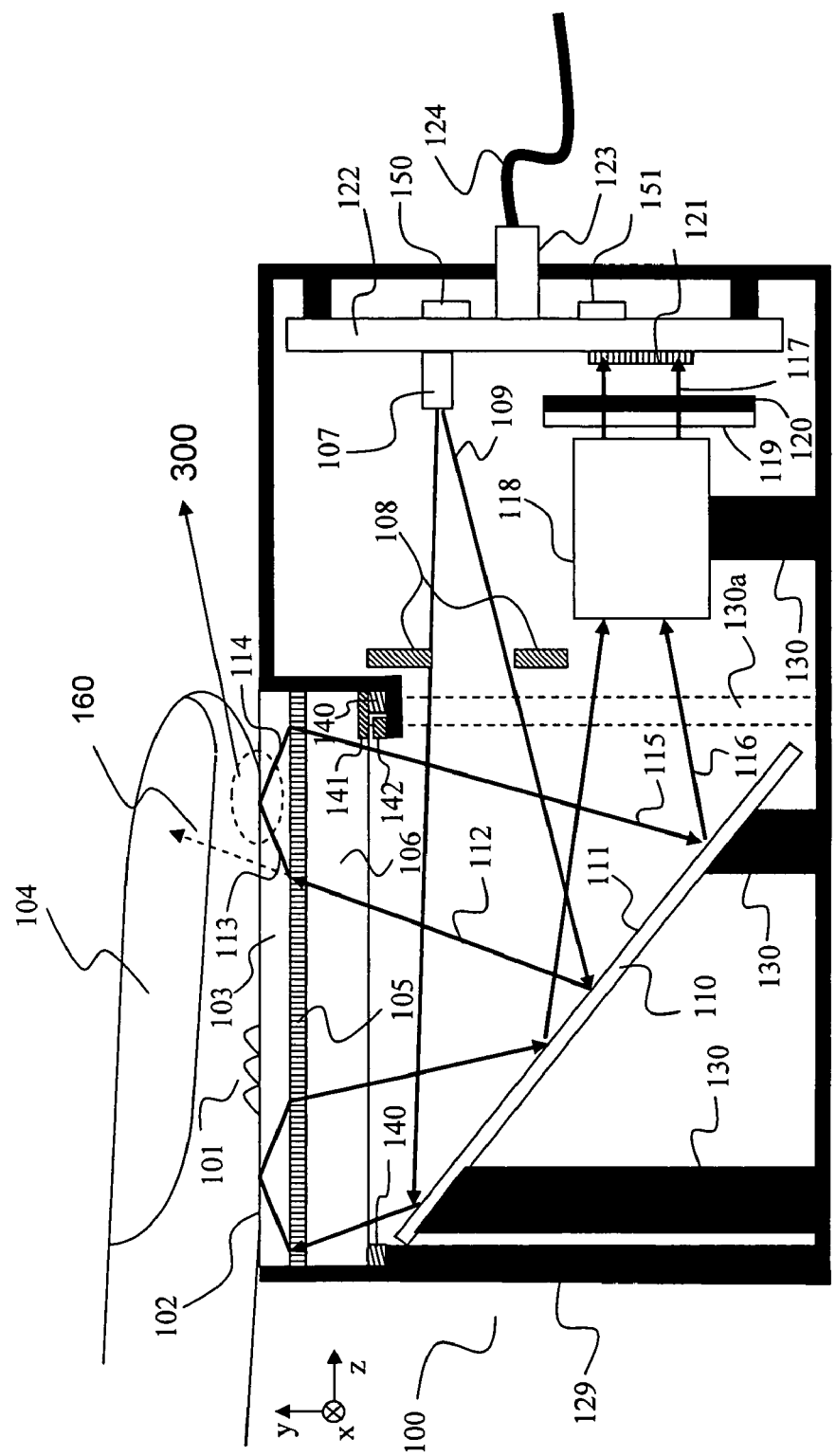
FIG. 1 is a schematic diagram of one embodiment of the apparatus of the present invention.

A description of preferred embodiments of the invention follows.

The apparatus of the present invention comprises an illumination system, with an illumination source and optical elements for beam shaping and for directing the light from the illumination source, a skin-contact window that acts as a skin-contact surface, an imaging system comprising optical elements for beam shaping and directing the light reflected from the skin-contact window and for imaging said light to a detector, and optionally an image processing system.

The illumination system comprises an illumination source and optical elements for beam shaping the light from said source. The illumination source may be, by way of example, at least one coherent or monochromatic light source, or at least one incoherent light source, one or more of at least one laser, light-emitting diode (LED), tungsten lamp, or fluorescent lamp. The preferred illumination sources are compact, efficient (require low power), and inexpensive such as a semiconductor laser or an LED. The illumination source may optionally be arranged as a grouping of LED elements or laser elements, or combinations thereof, so as to homogenize the intensity of the illumination over the area from which the image of the skin surface is to be obtained. Said illumination system also incorporates one or more optical elements for the beam shaping of the illumination system's radiation source. Said beam shaping, by way of example, uses optics that include at least one diffractive optical element (DOE) as a first DOE, referred to herein as the Illuminating or Illumination DOE, and optionally uses other optics such as one or more refractive, or reflective optical elements or combinations thereof.

In one embodiment of this invention, the beam shaping optics of the illumination system comprises an Illumination DOE and a reflective fold-mirror. Other combinations of diffractive, refractive and reflective optical elements are also contemplated by this invention. The Illumination DOE in one embodiment preferably collimates at least one radiation point source of the illumination system and additionally directs the at least one diffracted collimated beam towards the skin-contact surface or window. An apparatus of this invention that optionally incorporates an illumination system comprising diffractive optical elements (DOEs) and a plurality of sources, preferably comprises DOEs that are a combination of volume holograms that may be physically distinct and/or colocationally multiplexed in the same volume of the DOE material. In this manner, the volume holograms can efficiently combine multiple sources of the illumination source into a single beam of a desired wavefront that can be used to illuminate the skin area under examination. When the illumination system of this invention comprises one source, then a single hologram may be used as the Illumination DOE.

In one embodiment of the present invention, the at least one Illumination DOE has substantially the same diffraction efficiency across its clear aperture and its optical prescription and position are preferably determined in accordance with the numerical aperture and uniformity profile of the illumination source such that a beam of reasonable uniformity illuminates the region of skin to be examined. In an alternative embodiment, the diffraction efficiency of the at least one Illumination DOE is non-uniform and the non-uniformity in said efficiency is preferably the inverse match to the non-uniformity of the projected illumination source. In this manner the DOE-based illumination system is able to transform a nonuniform optical beam from the illumination source and create a region of uniform illumination for illuminating the skin topology.

The skin-contact surface or window forms the superstrate surface of an optically transparent substrate. The area of the window is preferentially at least as large as a typical thumbprint or is at least larger than the area of the skin surface that is to be imaged, and, by way of example, may be large enough to correspond to at least an area for the skin surface of more than one finger or thumb. Although not required by the current invention the surface is often planar. Optionally, the skin-contact window can have curvature to aid in illuminating and/or imaging the skin surface of at least one finger or thumb. In typical embodiments of the invention, light from the illumination system is directed by the Illumination DOE through the substrate to the skin-contact window with an incident angle at the superstrate surface that is large enough for total internal reflection (TIR) at the window-to-air interface.

The imaging system of the present invention comprises optical elements for beam directing and shaping light reflected from the skin-contact window, and an image capture device. The beam directing and shaping optics includes at least a second DOE, referred herein as an Imaging DOE, and use of other optics such as one or more reflective and refractive optical elements or combinations thereof is also possible. In one embodiment, the Imaging DOE diffracts the light incident to it from the Illumination DOE, and which is reflected from the skin-contact window or superstrate layer thereon, and said Imaging DOE thereby redirects and partially focuses said light that has reflected from the surface of the skin-contact window or superstrate layer thereon. The redirected light from said Imaging DOE is, by way of example, additionally directed through a conventional refractive lens system, comprising at least one lens element, or optionally through a diffractive lens system or combinations thereof, and onto the focal plane of the image capture device. The Imaging DOE in combination with one or more reflective, diffractive or refractive optical elements, or combinations thereof, can operate so as to focus and thereby demagnify the skin area onto the image capture device. Said demagnification can be by one demagnification ratio, $A_I/A_F$, where the ratio has a value less than 1.0 and where $A_I$ is the area of the captured fingerprint image on the sensor and $A_F$ is the area of the skin area on the superstrate layer. Alternatively, said demagnification can be selected from a group of at least two different demagnification ratios, $A_{I1}/A_F$ and $A_{I2}/A_F$. In yet another embodiment, the demagnification value $A_I/A_F$ may represent a continuum of values such as those that range from $A_{I\_min}/A_F$ to $A_{I\_max}/A_F$.

The image capture device of the imaging system of the present invention is, by way of example, typically at least one solid state CCD or CMOS detector array. The detector(s) captures the image which is typically converted to a digital form of the image. The captured image optionally is uploaded to a computer for image storage and, additionally, image analysis may be carried out on said uploaded images.

The described imaging system of the apparatus of this invention collects the light that is reflected from the skin-contact window or superstrate layer thereon and images it onto a sensor. When skin with topological structure such as friction ridges in finger and palm prints is pressed against the skin-contact window or superstrate material thereon, raised portions of the skin will make direct contact with the said window or superstrate material and an air gap will form between recessed portions of the skin topological structure and said window or superstrate material. Direct skin contact at the surface of the skin-contact window or superstrate material prevents TIR of the illumination light so that light that strikes these skin-contact regions partially transits the window-to-skin interface or superstrate layer-to-skin interface and is absorbed and scattered by the skin. In contrast, light that strikes the surface of the superstrate layer at air gap regions, such as those corresponding to recessed portions of the skin topological structure comprising valleys and/or pores, undergoes TIR at the window-to-air or superstrate material-to-air interfaces and is imaged by the imaging system onto the image capture device or detector.

It is preferable that light reflected from the skin surface, or the interface of the window or superstrate layer and raised portions of the skin topology that contact said window or superstrate layer, is not imaged onto the sensor. One method of minimizing reflectivity at the interface of the window or superstrate layer and raised portions of the skin topology is to select a material for the window, or a layer of material for coating the window, that has a refractive index that closely matches the index of refraction of skin.

Said imaging system of the apparatus of the present invention is in general composed of a single or a plurality of optical elements wherein each optical element can be refractive, diffractive, or reflective. In one embodiment, the imaging system is composed of an Imaging DOE and at least one additional optical element. In alternative embodiments the Imaging DOE may operate to diffract light incident on said DOE to a preferred direction whereupon imaging is carried out with one or more refractive or diffractive optical elements or combinations thereof. In further embodiments, the imaging DOE may be translated so that light directed by the illumination DOE reflects internally at least twice, such as once at the superstrate surface of the skin-contact window and once at the opposing substrate surface, so as to translate the reflected light that is to be imaged by an amount that substantially separates it from ambient light that otherwise may transmit into the imaging DOE and onto the image capture device. In a preferred embodiment, said Imaging DOE is designed to redirect the reflected light from the window or superstrate layer such that it propagates at an angle substantially normal to said interface.

The Imaging DOE, in addition to redirecting said reflected beam, may optionally have optical power such that it focuses the reflected beam. The Imaging DOE preferentially acts as a field lens and thereby diffracts the incident light onto said DOE into a focused cone of rays that are imaged by at least one additional optical element such as a second set of optics that may be reflective, refractive or diffractive, or combinations thereof. In one embodiment the second set of optics has one optical power, whereas in another embodiment it may have more than one optical power and may have a continuous or variable range of optical powers, much like a zoom optical system, or it may have discrete additional optical powers. In this manner, the imaging optical system can image a large area of the skin, and by using at least one demagnification the other imaging optics, such as a second set of optics, can be appreciably smaller in diameter than the object area being imaged. The imaging DOE acting as a field lens in combination with one or more refractive and/or diffractive optical elements can operate so as to demagnify the skin area by one or more demagnification ratios, $A_I/A_F$, where the ratio has values less than 1.0 and where $A_I$ is the area of the captured fingerprint image on the sensor and $A_F$ is the area of the skin area on the skin contact surface.

Variations of the present invention can be implemented to enhance performance. For example, light can be directed to the skin-contact window or superstrate material thereon at an incident angle that is large enough for TIR at the window-to-water or superstrate material-to-water interface (water can also include water comprising salts such as from sweat) but not large enough for TIR at the window-to-skin or superstrate material-to-skin interface. This embodiment is advantageous in that condensed water, such as from sweat, does not distort the imaging of the skin topology, in particular the pore structures and friction ridge topology. In addition the illumination system can direct light to the skin-contact window or superstrate material thereon at an incident angle that is large enough for TIR at the window-to-skin-oil or superstrate material-to-skin-oil interface but not large enough for TIR at the window-to-skin or superstrate material-to-skin interface. This embodiment preferably eliminates interference from latent prints caused by skin oil deposited on the contact window or superstrate material thereon.

Reduction of reflections at the window-skin or superstrate material-to-skin interface can increase image contrast. One method of minimizing this reflectivity is to choose a superstrate layer material that has an index of refraction that matches the index of refraction of skin as closely as possible. In another embodiment, the skin-contact window surface is coated with a thin-film coating that is designed for low reflectivity for a window-skin interface or for improving optical contact between the raised portion of the skin topology and the window surface. A film that is elastomeric and/or has hydrophilic chemical structure at the surface can be used to improve said optical contact. These coatings can be intended for permanent use, such as those that may be sputtered or deposited onto the surface, or chemisorbed to the surface, or alternatively they can be films of materials that are applied to the window surface. Said materials can, by way of example, be single-use layers that are disposed in a stack of thin films, the bottom layer of said stack disposed so as to contact the window, wherein the superstrate layer in the stack can be peeled apart from the next lower layer in said stack. Alternatively, the single use said films are applied individually so as to contact the window and are preferably removed prior to placing the next said film onto the window. Said materials can preferably be removed, either from the next layer in said stack or from the window material, such that residual organic and/or inorganic material deposited from the skin or from the layer itself is not present on the superstrate surface, said surface being either the next layer in said stack or the window material, or if it is present then it does not cause imaging of latent fingerprints. Additionally, said material can protect the window material from deposits of chemical compounds from the skin surface, thereby preventing formation of latent prints of the skin topology which can otherwise contaminate the surface and thereby compromise the fidelity of captured images of the skin topology.

Additionally the imaging apparatus of this invention can use two or more wavelengths for another aspect of the illumination system that instead illuminates the skin contact surface at angles less than the angle for TIR. Light from the at least two wavelengths that is diffuse reflected from areas of the skin topology that contact the skin surface is then imaged to a detector wherein the ratio of diffuse reflectivity for the at least two wavelengths is determined to analyze whether the skin topology is from a live finger. For instance reflectance from skin of a live finger at a wavelength of about 650 nm will be about two times greater than reflectance from a live finger at about 550 nm, and about 1.5 times greater than reflectance from a live finger at about 500 nm. The optimal ratios of reflectance of specific wavelengths in the visible region, to make a determination of the finger being a live finger, can be selected by those experienced in the art and, by way of example, the spectral reflectivity versus wavelength characteristics of skin can be found in the publication "Understanding the color of human skin", Eli Angelopoulou, GRASP Laboratory, University of Pennsylvania. The entire teachings of this publication is herein incorporated by reference. The spectrum of skin is closely related to chromophores in the skin, and thus spectrum of fingers that are not live will not exhibit reflectivity bands at 540 nm, 580 nm and 630 nm (see L.A. Brunsting, C. Sheard, "The color of the skin as analyzed by spectrophotometric methods: II. The role of pigmentation", The Journal of Clinical Investigation, Vol. 7, pp. 574-592, 1929, the relevant portions of which is herein incorporated by reference). Additionally, the dermis contains blood vessels and thus absorption spectrum of skin exhibits characteristic absorption bands at 420 nm and in also in the 545-575 nm range due to the presence of oxygenated hemoglobin, provided the skin is not heavily pigmented.

In one embodiment of this invention, the Illumination DOE and the Imaging DOE are placed in a plane parallel to the window of the imaging apparatus but sufficiently far from said window such that in relationship to the angle and size of the beam of light that propagates within the window material and illuminates the skin under examination, these two DOEs can be spatially separated from each other. In this embodiment, baffles and apertures can optionally be used such that no light from illumination source can escape the imaging apparatus. In a second embodiment, these DOEs are alternatively placed close enough to the window such that they are substantially overlapping. For this second embodiment, light may escape the imaging apparatus due to DOEs that are not 100% efficient, meaning that their diffraction efficiency is not 100%. Optionally with this second embodiment, as well as with the first embodiment, the imaging apparatus of this invention can be designed such that only when skin covers or presses against the window, does the reader system allow (through shutters or by turning on power to the illumination source) light to illuminate the window. In the said second embodiment, the two DOEs can be fabricated in two separate optical elements or combined into the same DOE media layer sandwiched by one pair of substrates. Since the light rays of a reader system with overlapping DOEs must pass through both DOEs when illuminating the skin, and through both DOEs upon reflecting at the skin-window interface, it is preferential that said DOEs are volume diffractive elements such as those fabricated, by way of example, using photopolymerizable materials or photorefractive crystals. Bragg diffraction characteristics can be optimized when using volume gratings for the DOEs such that the holograms have theoretically 100% diffraction efficiency for light propagating in one direction versus another. For the embodiment wherein the DOEs are spatially separated, these DOEs may be volume holograms, but may also be, by way of example, surface-relief gratings, since the requirement of high-efficiency gratings is not as critical when the light rays of the imaging apparatus propagate through each DOE only once.

The second set of imaging optics is preferentially designed such that in conjunction with the design of the Imaging DOE, a location for an aperture stop is fixed. Said aperture stop may, for example, be located between the Imaging DOE and the second set of imaging optics or may be located between one or more optical elements that comprise the second set of imaging optics. Said aperture stop is a preferred component of the reader system in that the acceptance diameter of the aperture stop controls the numerical aperture of the scattered light reflected from the skin and thereby its diameter affects the performance of the overall optical system.

Said second set of imaging optics, whether for one optical power or a grouping or range of optical powers, is also preferentially designed such that the image space is telecentric. In this manner, slight errors in placement of the detector with respect to the image plane result in a minimal magnification error. When the image space is telecentric it preferably allows a sharp notch filter to be incorporated into the optical system near the image plane. Said notch filter preferably allows only the wavelengths of the light from the illumination source to be imaged at the detector plane and rejects other light that may enter the system such as from the ambient environment of the reader system. Examples of such notch filters may include those comprising dichroic layers for filtering visible wavelengths, such as those made with layers of $TiO_2/SiO_2$, and also for filtering near infrared wavelengths. Other suitable filters may be absorbance type which transmit the desired wavelengths and absorb the wavelengths that are preferably not to be detected. The more confined the angles of incidence are on a notch filter, the sharper the cutoff can be.

Similarly, for the purposes of contrast enhancement, the illumination source is preferentially polarized and in such cases a linear polarizer is preferably placed in the imaging system to serve as an analyzer of the light being reflected from the skin. Skin, being a volume scatterer, will depolarize the beam, so by accepting only light into the detector that is of the original polarization of the illumination source, the contrast of the collected images of the skin can be maximized. Said linear polarizer, by way of example, may be a separate optical element, a polymer sheet that is laminated to the notch filter of the optical system if one is present, or incorporated into the cover window of the detector, or the diffraction characteristics of the Illumination and/or Imaging DOE may serve to achieve the desired polarization filtering.

The detector of the optical system is preferentially composed of a two-dimensional (2-D) array of photosensitive elements of sufficient density and number such that the electronic image collected has the desired resolution and size. The signal from the detector array that codes the 2-D electronic image of the skin topology may be passed directly out of the reader system to another electronic system capable of processing the data, but preferentially the reader system itself is able to perform some initial data processing. This data processing may entail numerous image processing algorithms that, by way of example, can include rotation, flipping, thresholding, equalization, subsampling, and binning. The imaging apparatus may also contain memory and additional CPU power to do direct comparisons of the skin topology features and to make certain classification and/or identifications of said skin topology Referring to FIG. 1, imaging apparatus 100 is depicted that is capable of imaging skin topology. The skin topology 101 to be imaged is placed on the window 103 of the imaging system. As illustrated, skin topology 101 being imaged is the fingerprint of a finger 104, but the apparatus of the present invention is not restricted to fingerprints and may be used to image other surface topology, which by way of example, may include palm prints and toe prints. The imaging system contains an illumination source 107. Illumination source 107 can be, but is not restricted to, at least one laser diode, or LED, or filament lamp, or fluorescent lamp. Illumination source 107 is preferentially a high-efficiency point source such as an LED or a laser diode, as will be discussed in further detail below. Ray 109 from the illumination source 107 passes by optional aperture 108 that controls the numerical aperture (NA) of the illumination source and is then reflected, by way of example, from fold mirror 110 that is supported by mechanical mounts 130. Although not required for the present invention, fold mirror 110 allows the imaging apparatus to be more compact. Fold mirror 110 has surface 111 that is preferably highly reflective at the wavelength or wavelengths of emission of illumination source 107. Ray 109 is therefore reflected off of surface 111 and reflected ray 112 passes through substrate block 106 and into the at least one diffractive optical element that is located in the grating region 105. Substrate block 106 is composed of material that is substantially transparent to wavelengths of the illumination source.

Figure 2:
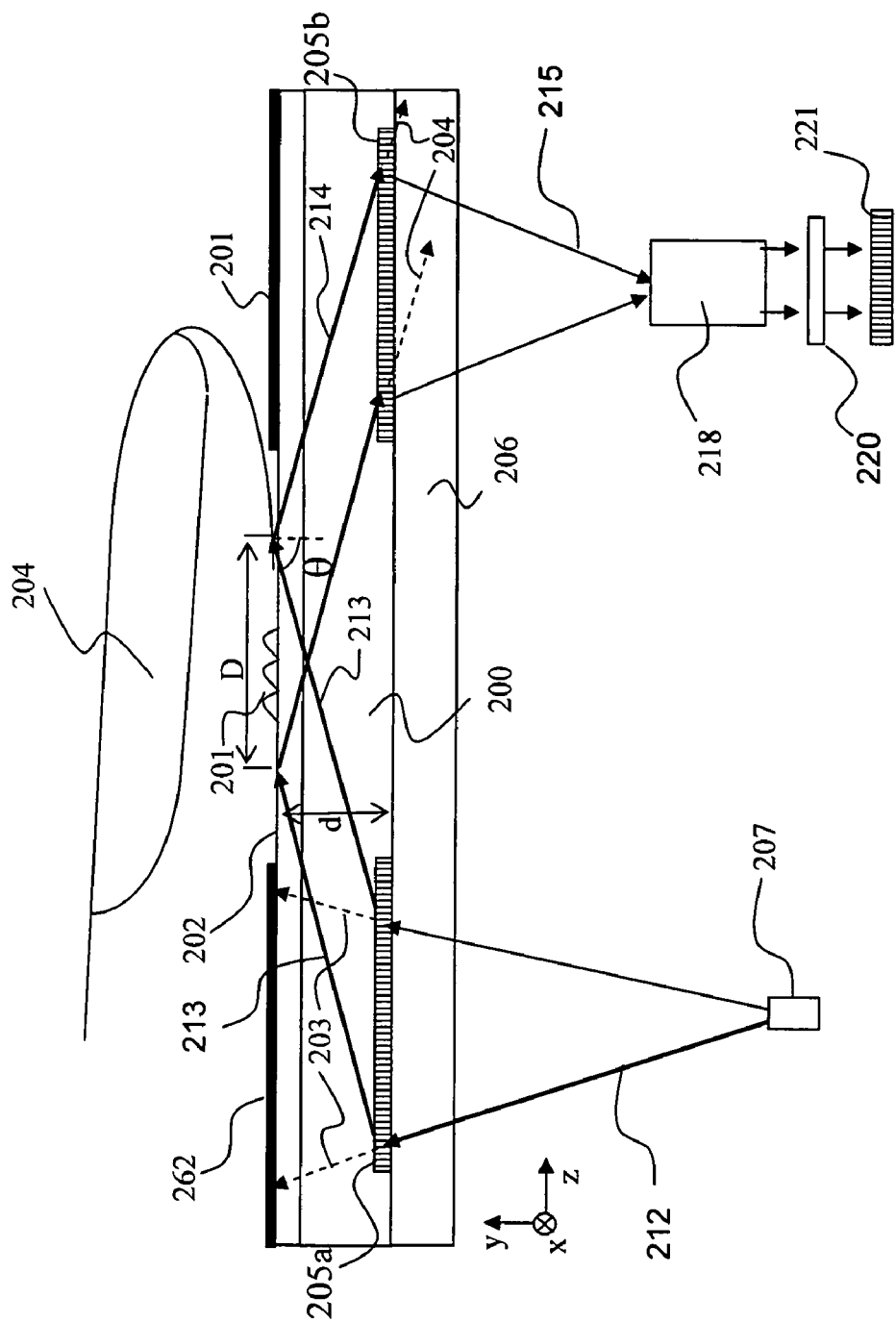
FIG. 2 shows a portion of an embodiment of a device of the present invention that employs spatially separated DOEs.

Referring to FIG. 2, in one embodiment, the imaging apparatus of the present invention comprises two diffractive optical elements (DOE), referred to as Illumination DOE 205a and Imaging DOE 205b. The diffractive optical elements are, by way of example, preferably holographic optical elements. Illumination DOE 205a is designed to diffract the light incident upon it (ray 212) and collimate it, and thereby direct the resultant collimated light (ray 213) towards skin-contact surface 202 at an angle with respect to window 200. Imaging DOE 205b of the present invention is designed, by way of example, to accept light reflected (ray 214) from skin-contact surface 202 and diffract ray 214, and thereby redirect it to imaging optics 218. As used herein, the term "imaging optics" describes one or more optical elements that focus rays reflected from skin-contact surface 202 onto image detector 221.

The Illumination and Imaging DOEs may be surface-relief or volume holograms. In one embodiment, the gratings are spatially overlapping. It is preferable that the gratings of the Illumination and the Imaging DOEs be volume holograms. With reference to FIG. 2, the reconstruction conditions of Illuminating DOE 205a and Imaging DOE 205b are preferably such that the Illuminating DOE 205a can only reconstruct the wavefront of the light from illumination source 207 (ray 212 being diffracted into ray 213), while the Imaging DOE 205b can only reconstruct the wavefront of the light reflected from the skin-contact surface 202 (ray 214 being diffracted into ray 215). This property eliminates cross-talk between the DOEs that would exist if the holograms were alternatively formed by surface-relief gratings.

With reference to FIG. 2, the two volume DOEs may comprise gratings that are spatially separated in y or z directions (as shown) or they may be co-locationally multiplexed volume gratings.

The HOEs can be recorded, for example, in low shrinkage photopolymerizable recording media produced by Aprilis, Inc. (Maynard, Mass.).

Figure 3:
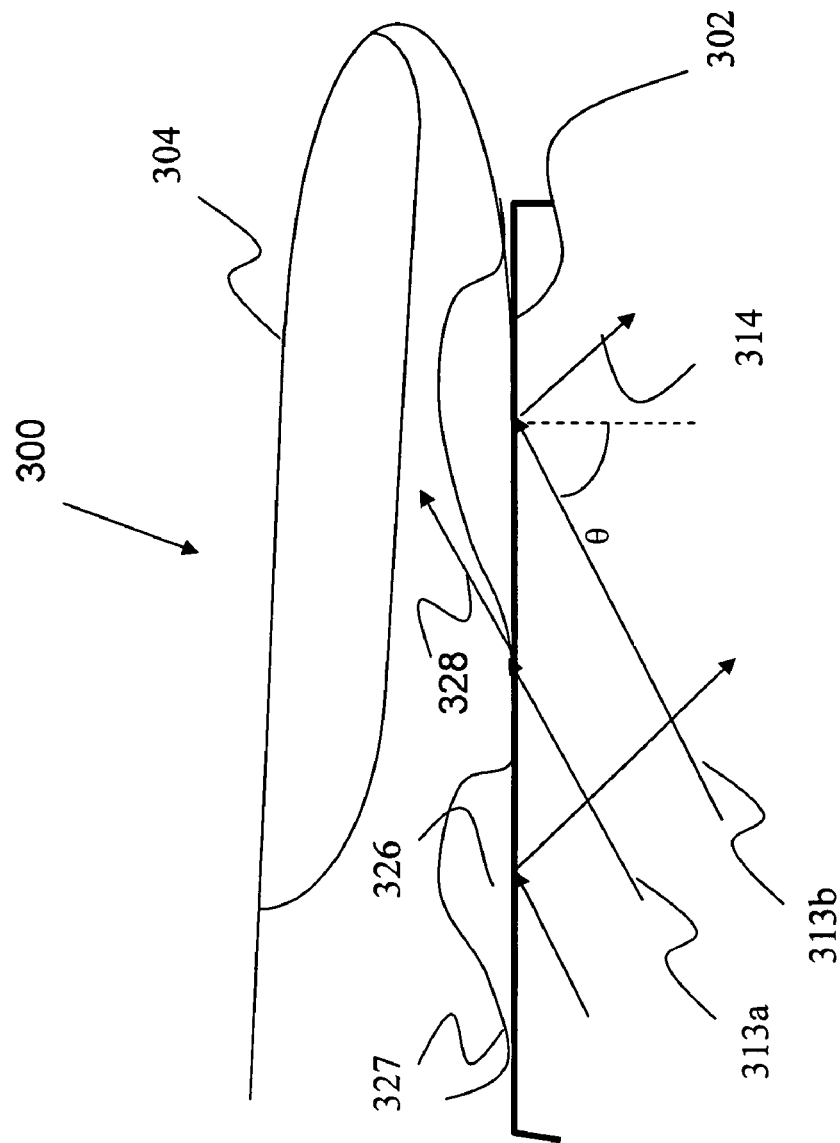
FIG. 3 is an illustration of a portion of a device of FIG. 1.

Referring to FIG. 3, image contrast is optimized in the captured fingerprint obtained with the apparatus of the present invention if the reflection of light from ridges 327 of the skin topology is minimized, while the reflection of light from valleys 326 and pores of the skin topology is maximized. This may be further advantageously accomplished by applying a coating, such as a hydrophilic coating, to the skin-contact surface 302 that improves the degree of optical contact for ridges 327. Alternatively, one can use a window material that has an index of refraction that as closely matches the index of refraction of the finger as possible as a method of suppressing reflections from ridges 327. Since skin has a relatively low index of refraction that is in the 1.38 to 1.43 range, suitable candidate materials for the window include, but are not limited to, silicones or low-index glass such as fused silica or Corning Pyrex™.

With reference to FIG. 2, the angle θ is the angle, which ray 213 makes with the normal to skin-contact surface 202. In one embodiment, the angle θ is near normal incidence, thereby making the device more compact in the z-direction (i.e. lateral direction).

In another embodiment, θ is an angle greater than the total internal reflection (TIR) angle for the interface between the material of skin-contact surface 202 and air. In this embodiment, the light from the illumination source (ray 213) does not escape out of the device, improving the contrast and reducing the eye safety hazard. Illumination ray 213 can only escape the material of skin-contact surface 202 if another material having the index of refraction greater than that of the material of skin-contact surface 202, such as skin, makes contact with skin-contact surface 202.

In another embodiment, the angle θ is set to an angle greater than the TIR angle for the interface between water and the material of skin-contact surface 202. In this embodiment, the skin-contact surface 202 has an index greater than 1.33. Consequently, light will not escape the material of skin-contact surface 202 if anything of index about 1.33 or lower is placed in contact therewith.

The advantage of this third embodiment is evident from the example of imaging a fingerprint where water vapor, such as from sweat, has collected between the ridges of the skin and/or is in the pores. If θ is smaller than the TIR angle for the interface between the material of skin-contact surface 202 and water, the fingerprint cannot be imaged since both the areas where the finger makes contact with skin-contact surface 202 and the areas where it does not allow light ray 213 to be transmitted out of the material of skin-contact surface 202. As a result, no light is reflected toward image detector 221 significantly impairing the contrast of the captured image. In another embodiment, the angle θ is larger than the TIR angle for the interface between the material of skin contact surface 202 and skin oil. According to G L Thomas and T E Reynoldson, in J. Phys. D: Appl. Phys, Vol. 8, pp 724-729 (1975), the relevant teachings of which are incorporated herein by reference, the refractive index of oils deposited from fingers is distributed in range of values between about 1.40 and 1.54 with the main portion of the distribution being in the range of values between about 1.42 and 1.52 at 551 nm. These values are consistent with the refractive indices of most of the long chain fatty material found in finger deposits. In this embodiment, if skin oil fills the ridges of the skin, image detector 221 will still be able to distinguish the contrast between the ridges and the valleys.

Note that for the embodiments described above, regarding incident angles θ having varying degrees of TIR, the upper bounds of the incident angles θ will be the angle that is TIR for the interface between the material of skin-contact surface 202 and skin.

It is preferred that light source employed by the device of the present invention be a point source, such as at least one LED or laser. With reference to FIG. 2, if illumination source 207 is a point source and a device of the present invention is designed so that light ray 213, illuminating a fused silica (n=1.46) skin-contact surface 202 totally internally reflects (TIR) when materials having an index of refraction less of than 1.34 is in contact with surface 202, then achieving TIR requires the angle θ 1A to be greater than 66.6°. To ensure that no TIR takes place when skin (lower bound of index of refraction equal to 1.38) is in contact with surface 202, however, requires that the incident angle of light ray 213 be less than 70.9°. Therefore, it is preferred that illumination source 207 be a point source or other source of a well-defined wavefront that can be collimated to better than 4.3°, thereby ensuring that the light illuminating surface 202 will undergo TIR for indices less than 1.34 but not for skin of index of refraction of 1.38.

Referring again to FIG. 1, if the Illumination DOE within grating region 105 is not 100% efficient, a portion of light ray 112 will not be diffracted, but continue to propagate as ray 160 towards skin contact surface 102 at an angle less than the TIR angle for that interface. In some embodiments, it may be desired that ray 160 be eliminated. Accordingly, in one embodiment, the device of the present invention is equipped with an optional system that detects when an object (e.g., a finger) is pressed against skin contact surface 102. One skilled in the art can design numerous systems capable of detecting the presence of an object pressed against a surface. In the example shown in FIG. 1, substrate block 106 is mounted to springs 140. When sufficient force is applied to skin-contact surface 102, a contact 141 makes contact with contact 142. Although not drawn, these two contacts may, by way of example, be wired to circuit board 122 in a manner such that they complete a circuit when the said two contacts touch each other. The electronics of circuit board 122, after detecting that said circuit has been completed allows the illumination source 107 to illuminate skin-contact surface 102. The illumination of surface 102 can be accomplished by providing for a shutter (not drawn) to open, wherein said shutter may, for example, be a mechanical or opto-electronic shutter, or alternatively by turning on the power to the illumination source.

Referring to FIG. 1, ray 114, reflected from skin-contact surface 102 is diffracted by the Imaging DOE within the grating region 105. Preferentially, the diffracted ray 115 propagates substantially normal to skin-contact surface 102. Additionally, the Imaging DOE preferably also focuses the beam of rays 115, thereby serving as a field (objective) lens for the imaging system. Diffracted ray 115 is reflected by fold mirror 110, thereby forming ray 116 that is directed into imaging optics 118. Imaging optics 118 includes one or more lens elements configured to relay an image of the skin-contact interface (i.e. the image of skin topology 101) onto at least one two-dimensional (2-D) sensor 121 that is mounted on circuit board 122. As used herein, the term "lens element" refers to one or more elements having optical power, such as lenses, that alone or in combination operate to modify an incident beam of light by changing the curvature of the wavefront of the incident beam of light.

Preferentially, imaging optics 118 is designed to be telecentric in image space, thereby allowing sensor placement errors to result in minimal magnification error and reducing the angular requirements on optional spectral filter 119. Optional spectral filter 119 may be added to improve the contrast of the image by minimizing the amount ambient light, such as room light or sunlight, detected by 2-D sensor 121. Spectral filter 119 is preferentially designed to transmit light of the wavelengths emitted by light source 107 and filter out light of other wavelengths such as by absorbing and/or reflecting said light at other wavelengths. Examples of such filters may include those comprising dichroic layers for filtering visible wavelengths, such as those made with layers of $TiO_2/SiO_2$, and also for filtering near infrared wavelengths. Other suitable filters may be absorbance type which transmit the desired wavelengths and absorb the wavelengths that are preferably not to be detected such as by use of dye compounds. One skilled in the art can place a spectral filter elsewhere within the imaging system of the present invention, such as on the lower surface of substrate block 106 or on the skin-contact surface 102, in lieu of or in conjunction with spectral filter 119. Alternatively, a spectral filter can be placed between imaging optics 118 and 2-D sensor 121 such as by incorporation on the cover glass of the sensor 121 or as an element of the imaging optics 118. In another embodiment, surface 111 of mirror 110 can be constructed with a coating that reflects only the wavelengths and angles of incidence the illumination source and the illumination system are designed to produce.

Sensor 121 suitable for using in an apparatus of the present invention can be, for example, at least one solid state charge-coupled device (CCD) or complementary metal-oxide-semiconductor (CMOS) detector array.

In one embodiment, the contrast of the image is improved through polarization control. Since skin is a volume scatter, it will depolarize light that reflects from it. Therefore, to achieve the highest contrast between areas with skin contact, such as ridges 327 in FIG. 3, and areas without skin contact, such as 326 in FIG. 3, it is preferred that the light imaged onto 2-D sensor 121 of FIG. 1 be polarized.

Referring to FIG. 2, in one embodiment, source 207 may be inherently polarized (as is the case for some semiconductor lasers) or a linear polarizer (not shown) may be placed in front of source 207. Preferentially, the polarization of source 207 matches the polarization orientation that provides for maximum diffraction efficiency of the DOEs 205a and 205b.

In another embodiment, either Illumination DOE or Imaging DOE or both can be polarization-sensitive. Referring, for example, to FIG. 2, illumination DOE 205a can be polarization-sensitive and its diffraction efficiency for one polarization is very high (preferentially >90%), while its diffraction efficiency for the orthogonal polarization is low (preferentially <10%).

Generally transmission volume holograms and surface relief gratings are polarization sensitive, and thus diffraction efficiency of the hologram can be significantly reduced when reconstructing a hologram with, for example, p-polarized light, if the grating is designed for s-polarized light. Polarization insensitive volume holograms, however, can also be recorded in materials that are sufficiently thick or exhibit large refractive index modulation or combinations thereof, and such holograms can also be used in the apparatus of the present invention.

Alternatively, and referring now to FIG. 1, to filter the depolarized light reflected from skin, linear polarizer 120 may be placed between imaging optics 118 and detector 121. One skilled in the art can place polarizer 120 at other locations and even, for example, record Illumination and/or Imaging DOEs within garting layer 105 so that these DOEs are polarization sensitive and thereby behave as linear polarizers.

In another embodiment, depolarized light is filtered out by employing Imaging DOE 205b (FIG. 2) that is polarization-sensitive.

Referring to FIG. 1, the image captured by 2-D sensor 121 can be processed by image processing electronics 150 integrated into one or a plurality of circuit boards 122. Image processing electronics 150 can be programmed to perform image processing algorithms such as, but not limited to, flipping, rotating, subsampling, binning, and edge detection. The processed electronic image may be sent to an external computer (not shown) for further image processing or data storage or may be stored in one or more memory chips of the imaging apparatus depicted as element 151.

In one embodiment, in which the data is relayed to an external computer, the processed image may be sent to an external computer by using bulk connector 123 attached to circuit board 122 and data cable 124. Alternatively, the data can be transmitted wirelessly, such as by using any of the known protocols and, by way of example, a Wireless Local Area Network (WLAN). The apparatus of the present invention, such as device 100 depicted in FIG. 1, can contain an internal power supply such as a battery (not shown) or can receive the electrical power it requires from a cable that may be the same one as data cable 124. This can be achieved, for example, by using USB 2.0 or IEEE 1394 Firewire protocols. Alternatively, power supply can use a separate cable (not drawn) as is the case for CameraLink®.

As described above, Illumination and Imaging DOEs may comprise gratings that are spatially separated or co-locationally multiplexed. FIG. 1 depicts an embodiment where the DOEs are multiplexed and, accordingly, are recorded within the same physical volume. In another embodiment, and as illustrated in FIG. 2, Illumination and Imaging DOEs 205a and 205b may be recorded in two separate grating regions that may abut or, as depicted, are spatially separated by a distance along at least one axis. The two DOEs 205a and 205b can be spatially separated by having transparent region 200 of sufficient thickness. Region 200 can be composed of a material having the same or nearly the same index of refraction as the material of skin-contact surface 202. In this embodiment, light diffracted by the Illumination DOE 205a propagates through region 200 and the material of skin-contact surface 202 at approximately the same angle θ. In order for Illumination DOE 205a to be spatially separated from Imaging DOE 205b, it is preferable that the distance "d" between DOEs 205a and 205b and skin-contact surface 202 satisfy the following inequality $$d > D/(2 \tan \theta),$$

where D is width of skin-contact surface 202 to be illuminated (see FIG. 2).

To further separate the DOEs 205a and 205b and thereby aid additionally in stray light management, another embodiment of the invention requires that distance d satisfy the following inequality $$d > D/\tan \theta.$$

In this manner, the region of the skin being examined will not be directly above either Illumination DOE 205a or Imaging DOE 205b. Therefore, opaque layer 262 can be placed directly above Illumination DOE 205a. Opaque layer 262 will operate so as to block undiffracted light 203 from escaping the apparatus of the present invention.

Figure 4:
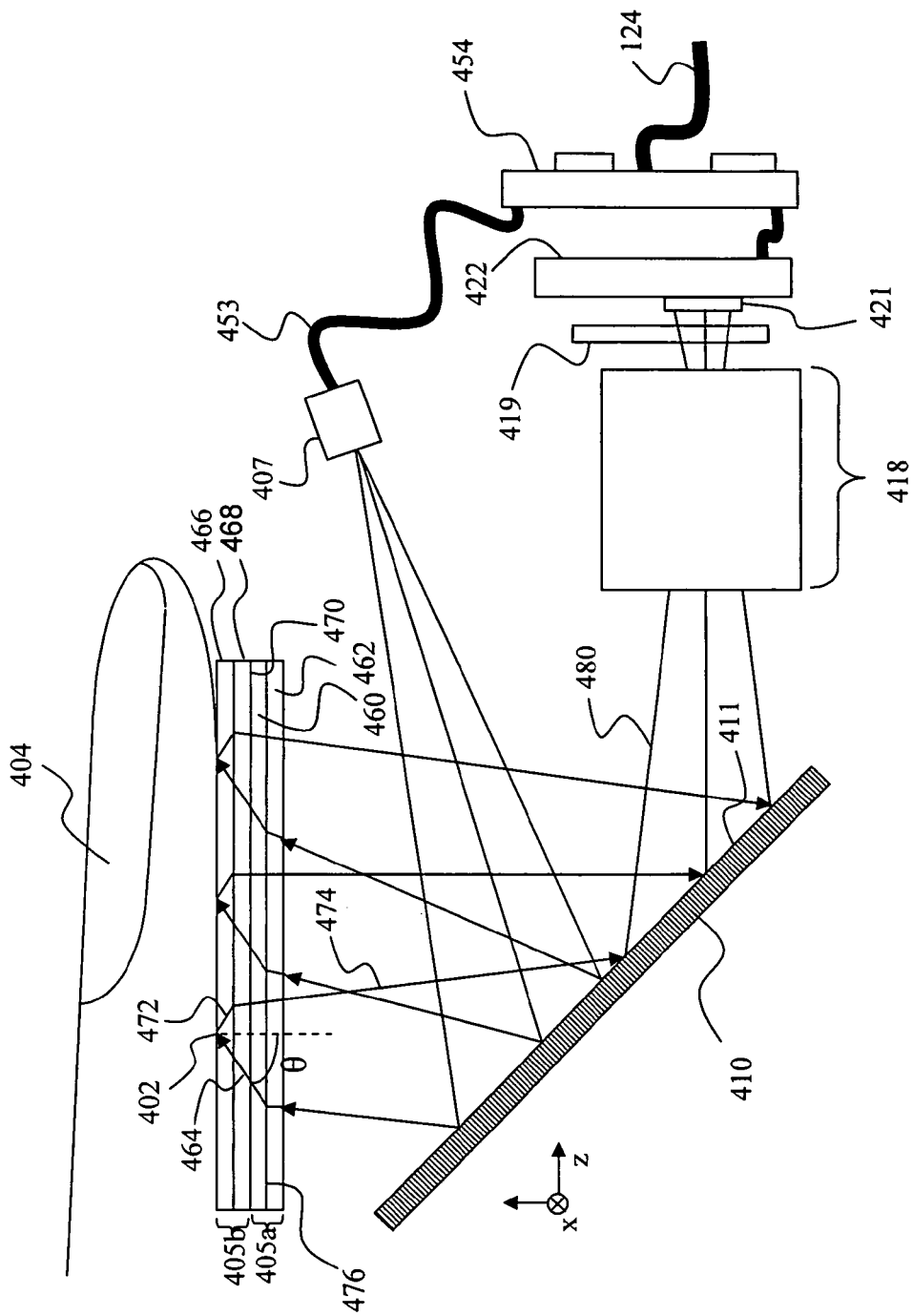
FIG. 4 is a schematic diagram of one embodiment of an imaging system of the present invention.

Although source 207 is depicted as being normal to substrate block 206, it may be oriented at an angle as shown with respect to light source 407 in FIG. 4.

Referring again to FIG. 2, in one embodiment, opaque layer 262 is preferentially placed above imaging DOE 205a such that light emanating from outside of the device does not enter region 200 and enter into imaging optics 218, which would otherwise introduce optical noise to the image detected by 2-D sensor 221.

In another embodiment, it is preferred that, as depicted in FIG. 2, light ray 204 (a ray undiffracted by imaging DOE 205b) propagates at an angle that does not allow it to enter imaging optics 218 and be detected by 2-D sensor 221. FIG. 4 illustrates an example of an optical system designed according to this invention to operate as a skin surface topology imaging system and to satisfy the imaging requirements as specified by the FBI AFIS (Automated Fingerprint Identification System) Level 2 Appendix F. (See also Revised Appendix F and Appendix G for Processing Flats (IAFIS Image Quality Specifications) for Electronic Fingerprint Transmission Specification. Revision: Apr. 5, 2004)

The embodiment of FIG. 4 employs illumination source 407 that comprises a single green InGaN LED (Model #NSPG500S from Nichia Corporation). The plastic lens of the LED (not shown) is ground and polished down flat such that the LED approximates a point source. LED source 407 is powered via cable 453 that is attached to controller board 454. Controller board 454 is configured to control sensor board 422 that includes 2-D sensor 421, drive illumination source 407 with the required current and voltage, and to supply a means of communicating with and means of accepting power from an external piece of equipment, which by way of example, may be a computer (not shown).

In a preferred embodiment, controller board 454 is designed to accept a USB 2.0 input, but may be designed for Firewire, wireless 802.11 g or a host of other communication protocols.

Referring to FIG. 4, illumination DOE 405a is fabricated by sandwiching a 50-μm layer of Aprilis (Maynard, Mass.) photopolymer material between two float glass substrates 460 and 462. Illumination DOE 405a is fabricated holographically by recording a wavefront with a doubled Nd:YAG laser ($\lambda$=532 nm) such that the diverging beam of the Nicchia LED of illumination source 407 (positioned approximately 100 mm from said Illumination DOE 405a) is collimated and directed at an angle of $\theta$=62.7° inside of float glass substrates 460 and 462 (of index 1.515 each). The angle $\theta$ of the light is chosen such that the illumination light (ray 464) would remain at TIR condition at the interface defined by skin contact surface 402 provided that a material of index of refraction less than 1.34 is in contact with skin-contact surface 402. In this manner, water condensing on surface 402 due to changes in temperature, humidity, rain, or sweat from a candidate's fingers will not impede the ability of the device to capture a fingerprint.

Illumination DOE 405a is glued, using a commercially available UV-curable adhesive (Norland 681, Norland Products, Cranbury, N.J.), to Imaging DOE 405b. Similarly to DOE 405a, Imaging DOE 405b comprises a sandwich of two float glass substrates 466 and 468. Preferably, glass substrates 466 and 468 encase a 25-μm layer or thicker layer of Aprilis photopolymer material.

The interface where the above-mentioned UV-curable adhesive is applied is interface 470. It is preferable that the UV-curable adhesive is index-matched to the substrates of imaging and illumination DOEs 405a and 405b, such that reflections at adhesive interface 470 are minimized.

Light ray 464 diffracted by Illumination DOE 405a passes directly through the volume grating of Imaging DOE 405b because ray 464 is not Bragg-matched to this grating. Ray 464, diffracted by illumination DOE 405a, illuminates skin-contact surface 402. Light ray 472, reflected from skin-contact surface 402 is directed towards the grating of Imaging DOE 405b.

Imaging DOE 405b is fabricated holographically by recording a wavefront with a doubled Nd:YAG laser ($\lambda$=532 nm) such that reflected beam or rays 472 propagating at 62.7° inside of float glass substrates 466 and 468 is redirected to propagate substantially normal to skin-contact surface 402 while being focused at a distance approximately 75 mm away from Imaging DOE 405b.

Since light ray 474 diffracted by Imaging DOE 405b is not Bragg-matched to the volume grating of Illumination DOE 405a that is located at interface 476 between glass substrates 460 and 462, diffracted ray 474 passes through Illumination DOE 405a unaffected.

Light ray 474 strikes reflective surface 411 of mirror 410 and is directed into imaging optics 418 (as rays 480). In one embodiment, imaging optics 418 includes a 25-mm focal length camera objective lens MV-250-25 from Optical Product Development (Lexington, Mass.) to image reflected image of the skin topology of finger 407 onto 2-D sensor 421. By way of example, an Eastman Kodak (Rochester, N.Y.) CMOS chip KAC-9648 (1288×1032 array of 6×6 μm pixels) can be used as said 2-D sensor. By adjusting imaging optics 418, a magnification of up to −0.2835 can be achieved, resulting in a device capable of capturing images of 27.3×21.8 mm skin areas at a digital resolution of 1200 ppi (points per inch).

In one embodiment, spectral filter 419 is employed in the optical path between imaging optics 418 and detector 421. Spectral filter 419 can comprise filter #5156 Fern Green from Rosco Laboratories (Stamford, Conn.) and filter IRC30 from Sunex Inc. USA (Carlsbad, Calif.). Said Rosco filter rejects visible light except light centered about 535 nm (i.e., it passes light of the Nicchia green diode being used). However, said Rosco filter transmits light in the near-IR band. Therefore, inserting Sunex filter is preferential as it has high transmission in the visible portion of the spectrum, yet cuts out wavelengths above 640 nm from reaching detector 421. In alternative embodiments the spectral filter 419 can be one dichroic filter element that comprises layers designed reject visible light except light centered about the desired wavelength of the illumination source as well as reject light in the near-IR band.

Figure 5:
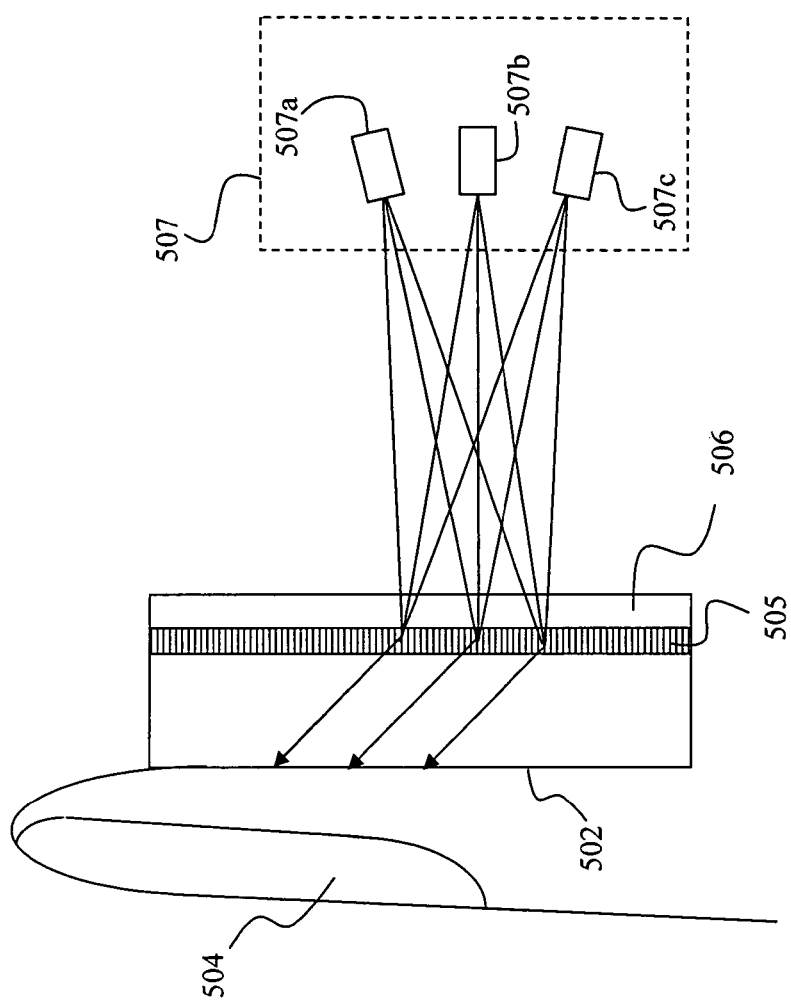
FIG. 5 is a schematic diagram showing one embodiment of the imaging system of the present invention that employs a plurality of light sources.

Another embodiment of the device of the presser invention is illustrated in FIG. 5. In this embodiment, illumination source 507 comprises a plurality of light sources 507a, 507b, 507c, etc. For clarity, the illustrated system does not have fold mirror 410 (as shown in FIG. 4). It should be understood, however, that one of more fold mirrors may be present between illumination source 507 and substrate block 506. In the specific example illustrated in FIG. 5, illumination source 507 is comprised of three light sources. Though three light sources are illustrated, any number of light sources can be used. The plurality of light sources that comprise light source 507 may be arranged in a line, but may also be arranged in 2-D or 3-D layouts.

Similarly to the embodiment depicted in FIG. 1, the embodiment of FIG. 5 includes grating region 505 that comprises multiplexed volume holograms that form Illumination and Imaging DOEs. When illumination source 507 comprises a plurality of light sources, the Illumination DOE located in grating region 505 preferentially combines light from the plurality of light sources and directs it towards skin-contact interface 502. It is therefore preferred that the light sources have low coherence such that interference effects of the combined light sources do not manifest themselves at skin-contact interface 502.

Preferably, the holographic grating located within grating region 505 includes a sufficient number of holograms to collimate and direct the light from the light sources (507a through 507c) to skin-contact interface 502. Preferably, these holographic gratings are co-locationally multiplexed.

Alternatively, grating region 505 may comprise spatially separated gratings, similarly to the embodiment depicted in FIG. 2. In this embodiment, each separate grating collimates and redirects light from a separate light source 507a through 507c.

EXEMPLIFICATION

Example 1

Optical Imaging Performance of the Imaging Apparatus Depicted in FIG. 4

Figure 6B:
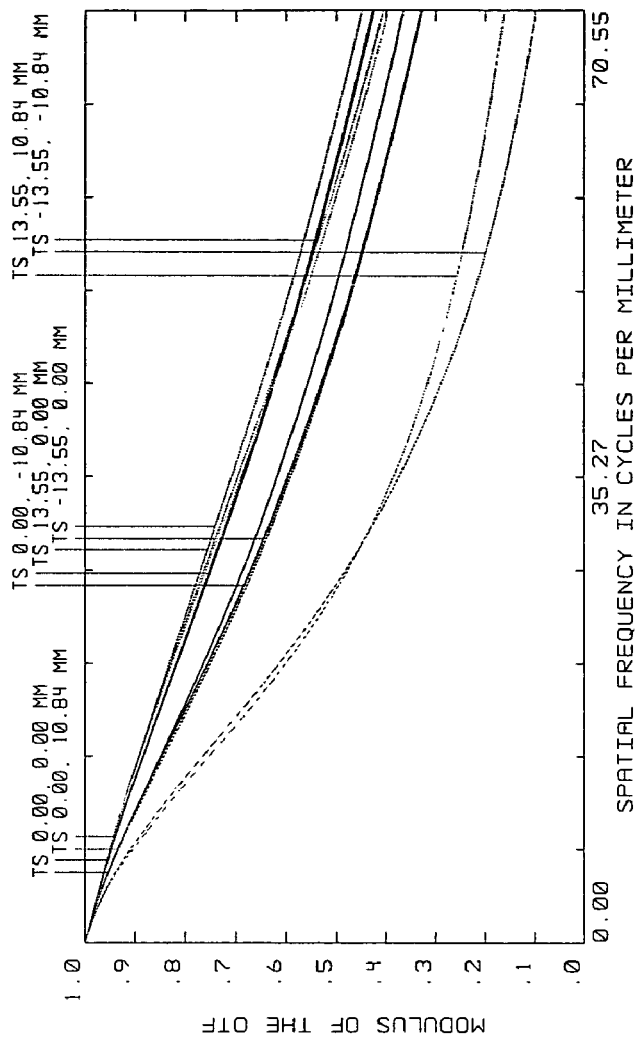
FIG. 6B shows the modulation transfer function (MTF) as a function of frequency for the system as modeled for FIG. 6A.
Figure 6A:
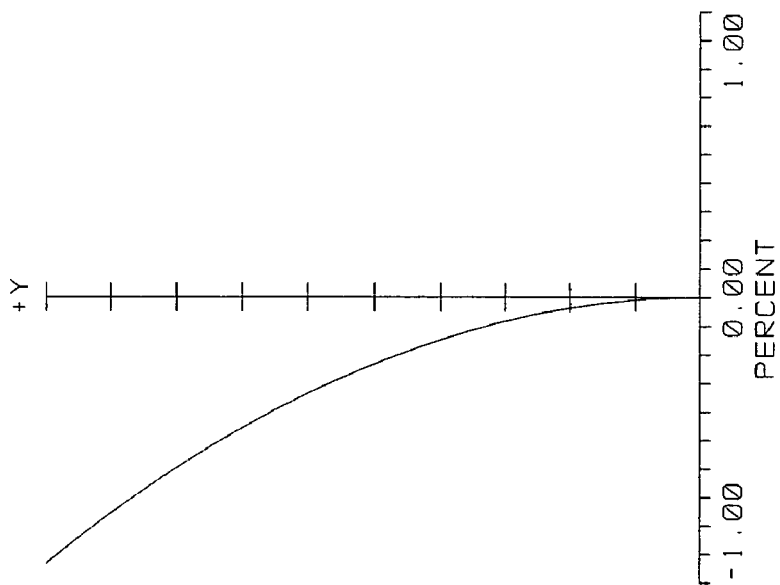
FIG. 6A shows the distortion as a function of field for one embodiment of the imaging system of the present invention.

FIG. 6A and FIG. 6B illustrate the optical imaging performance of one embodiment of the imaging apparatus depicted in FIG. 4. In this embodiment, substrates 460, 462, 468 and 466 were modeled as BK7 glass with thicknesses of 1.6, 1.6, 1.6, and 0.6 mm, respectively. The device was designed to achieve 1200 ppi electronic resolution with the use of an Eastman Kodak (Rochester, N.Y.) CMOS chip KAC-9648 (1288×1032 array of 6×6 μm pixels). The custom imaging optics have the prescription as shown in Table 1.

TABLE 1

Imaging Optics for Performance denoted by FIGS. 6A and 6B.

| Lens Element | Material | Parameters (mm) |
|---|---|---|
| 1 | LAK10 | R1 = 9.324 |
| | | R2 = −23.875 |
| | | T = 3.767 |
| Air gap | Air | T = 0.635 |
| 2 | SF8 | R1 = −13.760 |
| | | R2 = 5.425 |
| | | T = 1.259 |
| Air gap | Air | T = 5.206 |
| 3 | SK16 | R1 = −1555.9 |
| | | R2 = −8.637 |
| | | T = −8.637 |

The optical system was analyzed observing the performance of the system at field points with coordinates of 10.84 and 13.55, as these represents half of the full fields corresponding to a 1280×1024 CMOS sensor array operating at 1200 ppi. FIG. 6A illustrates the distortion of the system. The distortion does not exceed 1%, while the AFIS Level 2 specification for a 500 ppi fingerprint scanner is <1%. FIG. 6B illustrates the modulation transfer function (MTF) as a function of image-space frequency. Since the optical system has a magnification of −0.28346, a frequency of 35.27 Hz and 70.55 Hz in image space corresponds with 10 cycles/mm and 20 cycles/mm, respectively, in object space. The AFIS Level 2 specifications for a 500 ppi scanner require that a fingerprint scanner achieves MTF values of at least 0.925 for 1 cycle per mm (cy/mm), at least 0.677 for 5 cy/mm, at least 0.458 for 10 cy/mm, at least 0.287 for 16 cy/mm, and at least 0.210 for 20 cy/mm. FIGS. 6A and 6B show that the imaging system diagrammed in FIG. 4 satisfies the AFIS Level 2 500 ppi fingerprint scanner specifications for distortion and MTF.

Example 2

Optical Imaging Performance of the Imaging Apparatus Depicted in FIG. 4

Figures 7A, 7B:
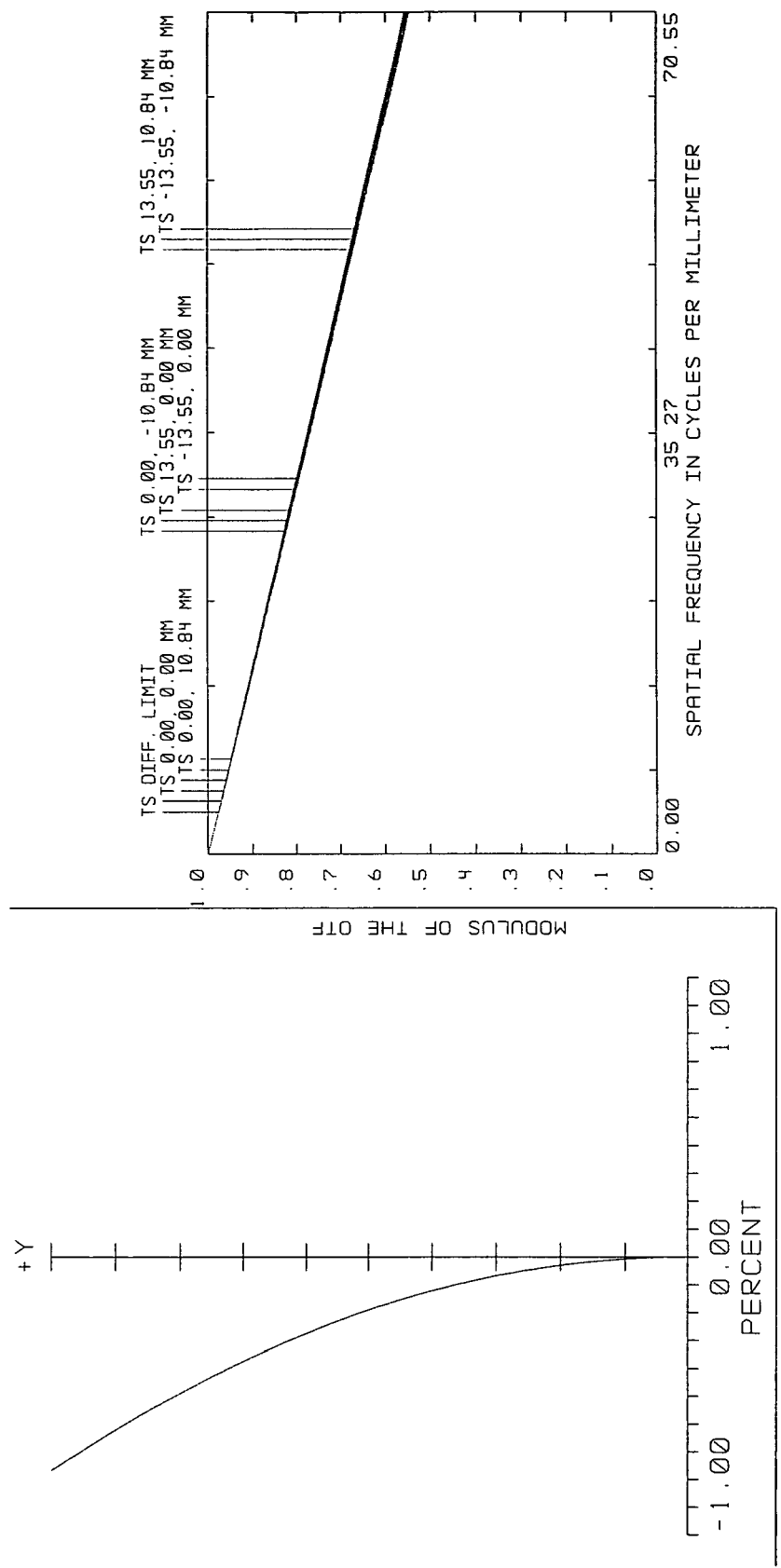
FIG. 7A shows the distortion as a function of field for one embodiment of the imaging system of the present invention.
FIG. 7B shows the modulation transfer function (MTF) as a function of frequency for the same specific reader system as modeled for FIG. 7A.

FIG. 7A and FIG. 7B illustrate the optical imaging performance of one embodiment of the imaging apparatus depicted in FIG. 4. In this embodiment, by use of a custom set of imaging optic 418, the imaging apparatus is capable of passing AFIS Image Quality Specifications for 1000 ppi. The substrates 460, 462, 468 and 466 were modeled as per above for BK7 glass with thicknesses of 1.6, 1.6, 1.6, and 0.6 mm, respectively. The custom imaging optics have the prescription as shown in Table 2.

TABLE 2

Imaging Optics for Performance denoted by FIGS. 7A and 7B.

| Lens Element | Material | Parameters (mm) |
|---|---|---|
| 1 | LAK10 | R1 = 9.265 |
| | | R2 = −18.779 |
| | | T = 3.767 |
| Air gap | Air | T = 0.635 |
| 2 | SF8 | R1 = −11.523 |
| | | R2 = 5.649 |
| | | T = 1.259 |
| Air gap | Air | T = 5.206 |
| 3 | SK16 | R1 = 1787.14 (cyl.) |
| | | R2 = −8.916 |
| | | T = −4.709 |

FIG. 7A illustrates the distortion of the system. The maximum distortion is 0.77% which slightly exceeds the AFIS Level 2 specification for a 1000 ppi fingerprint scanner that is <0.7%. To one skilled in the art, it is straight-forward to digitally correct the distortion level to bring the system in compliance with said AFIS Level 2 specification. FIG. 6B illustrates the modulation transfer function (MTF) as a function of image-space. Since the optical system has a magnification of −0.28346, a frequency of 35.27 Hz and 70.55 Hz in image space corresponds with 10 cycles/mm and 20 cycles/mm, respectively, in object space. The AFIS Level 2 specifications for a 500 ppi scanner require that a fingerprint scanner achieves MTF values of a least 0.925 for 1 cycle per mm (cy/mm), at least 0.677 for 5 cy/mm, at least 0.458 for 10 cy/mm, at least 0.287 for 16 cy/mm, and at least 0.210 for 20 cy/mm. FIGS. 7A and 7B show that the imaging system diagrammed in FIG. 4 satisfies the AFIS Level 2 500 ppi fingerprint scanner specifications for distortion and MTF.

Example 3

Fingerprints Taken with the Apparatus Depicted in FIG. 4

Figure 8B:
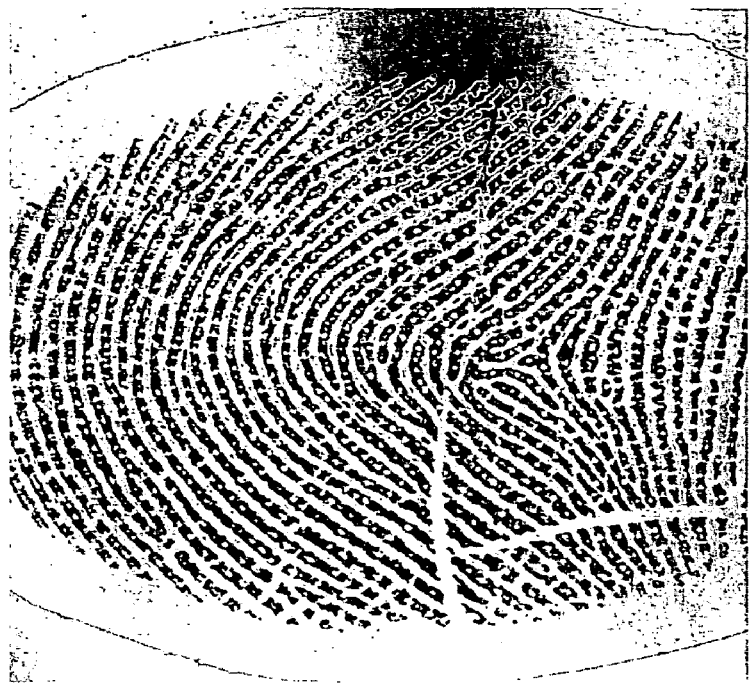
FIG. 8B illustrates the effect of salt water on fingerprint images acquired by an embodiment of the present invention as depicted in FIG. 2.
Figure 8A:
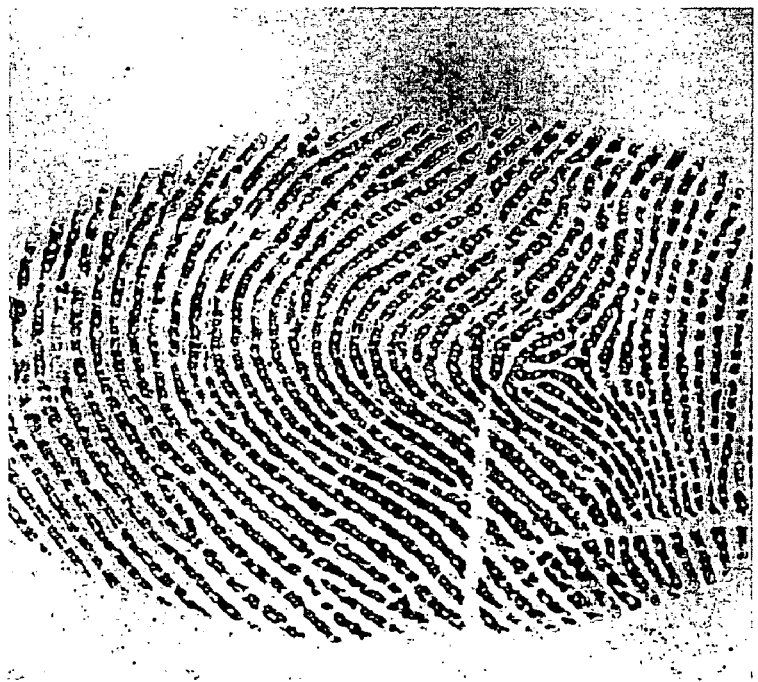
FIG. 8A shows a fingerprint acquired by an embodiment of the present invention as depicted in FIG. 2.

In FIG. 8A and FIG. 8B are images of fingerprints that were taken with the apparatus depicted in FIG. 4. FIG. 8A illustrates the fingerprint at 1200 ppi of a subject that was taken dry (i.e., no moisture added to the finger). The image captured is approximately 27.3×21.8 mm across. In FIG. 8B an image of the same finger was taken under the same conditions as the fingerprint in FIG. 8A with the exception that a saturated salt water solution was poured on skin contact surface 402. FIG. 8B illustrates the apparatus constructed as exemplification of embodiments of the present invention operates at a TIR angle that is higher than the TIR angle for float glass to salt water and in this manner fingerprints can still be taken of a substrate with sweaty hands and/or in a very humid environment.

While this invention has been particularly shown and described with references to preferred embodiments thereof, it will be understood by those skilled in the art that various changes in form and details may be made therein without departing from the scope of the invention encompassed by the appended claims.

What is claimed is:

1. An apparatus for acquiring an image of skin topology, comprising:
    at least one light source configured to form a source beam;
    at least one illumination diffractive optical element (DOE) disposed in the optical path of the source beam and configured to diffract the source beam, thereby forming an illuminating beam;
    a skin-contact surface disposed in the optical path of the illuminating beam and configured to at least partially reflect the illuminating beam at regions of a boundary between the skin-contact surface and skin not in contact with the skin-contact surface, thereby forming a reflected beam;
    a least one imaging diffractive optical element (DOE) disposed in the optical path of the reflected beam and configured to diffract, redirect and focus the reflected light beam, thereby forming an image beam; and
    a sensor array configured to receive at least a portion of the image beam and thereby to detect an acquired image.

2. The apparatus of claim 1, wherein the illumination DOE is configured to reconstruct the source beam, and the imaging DOE is configured to reconstruct the reflected beam.

3. The apparatus of claim 1, wherein at least one illumination DOE and at least one imaging DOE are spatially separated.

4. The apparatus of claim 1, wherein at least one illumination DOE and at least one imaging DOE are co-locationally multiplexed.

5. The apparatus of claim 1, wherein the illumination DOE is configured so that the illuminating beam totally internally reflects at the regions of the boundary between the skin-contact surface and skin that are not in contact with the skin-contact surface.

6. The apparatus of claim 5, wherein the skin-contact surface comprises a hydrophilic layer.

7. The apparatus of claim 5, wherein the skin-contact surface comprises a plurality of separable hydrophilic layers disposed in a stack.

8. The apparatus of claim 1, further including imaging optics disposed in the optical path of the image beam, said imaging optics configured to relay the image beam to the sensor array.

9. The apparatus of claim 8, wherein the imaging DOE focuses the image beam, thereby serving as an objective lens for the imaging optics.

10. The apparatus of claim 9, wherein the imaging optics has variable optical power.

11. The apparatus of claim 10, wherein the imaging optics relays an image beam of variable optical resolution to the sensor.

12. The apparatus of claim 1, wherein the illumination DOE is polarization-sensitive.

13. The apparatus of claim 1, wherein the imaging DOE is polarization-sensitive.

14. The apparatus of claim 1, further including at least one mirror configured to relay the source beam to the illumination DOE and to relay the image beam to the sensor array.

15. The apparatus of claim 1, further including a spectral filter disposed in the optical path of one or more beams selected from the group of the source beam, the illuminating beam, the reflected beam, and the image beam.

16. The apparatus of claim 15, wherein the spectral filter transmits light of the wavelengths emitted by the light source.

17. The apparatus of claim 16, wherein the spectral filter is a dichroic filter or an absorbance filter.

18. The apparatus of claim 1, further including a linear polarizer filter disposed in the optical path of one or more beams selected from the group of the source beam, the illuminating beam, the reflected beam, and the image beam.

19. The apparatus of claim 1, wherein the light source is selected from the group consisting of a laser diode, an LED, a filament lamp, and a fluorescent lamp.

20. The apparatus of claim 1, wherein the light source is a laser diode or an LED.

21. The apparatus of claim 1, wherein the at least one light source comprises a plurality of light sources.

22. The apparatus of claim 21, wherein said light sources have low coherence with respect to each other.

23. The apparatus of claim 1, further including a programmable processor programmed to perform image processing.

24. The apparatus of claim 1, further including data storage for storing acquired images.

25. The apparatus of claim 1, further including a detection system for detecting an object in contact with the skin-contact surface.

26. The apparatus of claim 1, wherein the sensor is a charge-coupled device (CCD) or complementary metal-oxide-semiconductor (CMOS) detector array.

27. A method of acquiring an image of skin topology, comprising:
    directing a source beam from a light source to at least one illumination diffractive optical element (DOE), thereby diffracting the source beam and forming an illuminating beam;
    directing the illuminating beam at a skin contact surface, configured to at least partially reflect the illuminating beam when the skin contact surface is not in contact with skin, thereby at least partially reflecting the illuminating beam and forming a reflected beam;
    directing the reflected beam to at least one imaging diffractive optical element (DOE), thereby diffracting, redirecting and focusing the reflected light beam and forming an image beam; and
    directing the image beam at a sensor array, thereby detecting the acquired image.

28. The method of claim 27, wherein the illumination DOE is configured so that the illuminating beam totally internally reflects at regions of a boundary between the skin contact surface and skin not in contact with the skin contact surface.

29. The method of claim 27, wherein the illumination DOE is configured to reconstruct the source beam, and the imaging DOE is configured to reconstruct the reflected beam.

30. The method of claim 27, wherein at least one illumination DOE and at least one imaging DOE are spatially separated.

31. The method of claim 27, wherein at least one illumination DOE and at least one imaging DOE are co-locationally multiplexed.

32. The method of claim 27, further including directing the image beam at imaging optics, thereby relaying the image beam to the sensor array.

33. The method of claim 32, wherein the imaging DOE focuses the image beam, thereby serving as an objective lens for the imaging optics.

34. The method of claim 32, wherein the imaging optics has variable optical power.

35. The method of claim 34, wherein the imaging optics relays an image beam of variable resolution to the sensor.

36. The method of claim 27, further including directing the source beam to at least one mirror, thereby relaying the source beam to the illumination DOE.

37. The method of claim 27, further including directing the image beam to at least one mirror, thereby relaying the image beam to the sensor array.

38. The method of claim 27, further including directing one or more beams selected from the group of the source beam, the illuminating beam, the reflected beam, and the image beam at a spectral filter.

39. The method of claim 38, wherein the spectral filter is a dichroic filter or a absorbance filter.

40. The method of claim 27, further including directing one or more beams selected from the group of the source beam, the illuminating beam, the reflected beam, and the image beam at a linear polarizer filter.

41. The method of claim 27 wherein at least one of the diffractive optical elements is polarization-sensitive.

42. The method of claim 27, further including performing image processing by a programmable processor.

43. The method of claim 27, further including storing acquired images in a data storage device.

44. The method of claim 27, further including detecting an object in contact with the skin contact surface by a detection system.

45. An apparatus for acquiring an image of skin topology, comprising:
light generating means for forming a source beam;
illuminating diffractive means, disposed in the optical path of the source beam, for diffracting the source beam and thereby forming an illuminating beam;
skin contacting means, disposed in the optical path of the illuminating beam, for at least partially reflecting the illuminating beam at regions of a boundary between the skin contacting means and skin not in contact with the skin contacting means, thereby forming a reflected beam;
at least one imaging diffractive means, disposed in the optical path of the reflected beam, for diffracting, redirecting and focusing the reflected light beam, thereby forming an image beam; and
detection means for receiving at least a portion of the image beam and thereby detecting the acquire image.

* * * * *